United States Patent [19]

Felix

[11] Patent Number: 4,511,394
[45] Date of Patent: Apr. 16, 1985

[54] SUBSTITUTED BENZYLOXY CHLOROETHOXY ETHANE HERBICIDE ANTIDOTES

[75] Inventor: Raymond A. Felix, Richmond, Calif.

[73] Assignee: Stauffer Chemical Co., Westport, Conn.

[21] Appl. No.: 478,389

[22] Filed: Mar. 24, 1983

Related U.S. Application Data

[62] Division of Ser. No. 244,453, Mar. 16, 1981, Pat. No. 4,400,204.

[51] Int. Cl.³ ............... A01N 37/34; A01N 37/18
[52] U.S. Cl. ............................. 71/105; 71/88; 71/94; 71/95; 71/100; 71/111; 71/118; 71/124
[58] Field of Search .................. 71/118, 105, 124; 260/465 F

[56] References Cited

U.S. PATENT DOCUMENTS

| | | | |
|---|---|---|---|
| 3,133,810 | 5/1964 | Hamm | 71/101 |
| 3,442,945 | 5/1969 | Olin | 71/118 |
| 3,814,807 | 6/1974 | Fan | 260/465 F |
| 3,886,283 | 5/1975 | Dory et al. | 71/105 |
| 4,283,221 | 8/1981 | Vogel et al. | 564/214 |
| 4,294,764 | 10/1981 | Rinehart | 71/118 |
| 4,336,058 | 6/1982 | Felix | 71/88 |
| 4,392,884 | 7/1983 | Pallos et al. | 71/100 |
| 4,411,686 | 10/1983 | Green et al. | 71/118 |

Primary Examiner—Glennon H. Hollrah
Assistant Examiner—Andrew Duff Meikle
Attorney, Agent, or Firm—Leona L. Lauder

[57] ABSTRACT

An herbicide antidote having the formula:

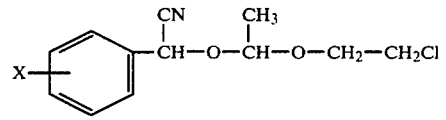

in which X is selected from the group consisting of hydrogen and halogen wherein the halogen is chlorine, bromine or iodine.

8 Claims, No Drawings

SUBSTITUTED BENZYLOXY CHLOROETHOXY ETHANE HERBICIDE ANTIDOTES

This application is a divisional of U.S. application Ser. No. 244,453 filed Mar. 16, 1981 now U.S. Pat. No. 4,400,204.

FIELD OF THE INVENTION

This invention relates to herbicide antidotes, and, more particularly, to certain substituted benzyloxy chloroethoxy ethane compounds which are useful as herbicide antidotes.

BACKGROUND OF THE INVENTION

An herbicide is a compound which controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species; See, for example, U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

Thiocarbamate and acetanilide herbicides are particularly effective in the control of grassy type weeds which interfere with the cultivation of a wide variety of crops, e.g., barley, corn, cotton, lentils, peanuts, peas, potatoes, soybeans, spinach, tobacco and tomatoes. Frequently the effective use of these herbicides requires the addition of an antidote compound.

DESCRIPTION OF THE INVENTION

It has now been discovered that certain benzyloxy chloroethoxy ethane compounds are effective antidotes for the protection of a variety of crops from thiocarbamate and acetanilide herbicide injury. These compounds have the following formula:

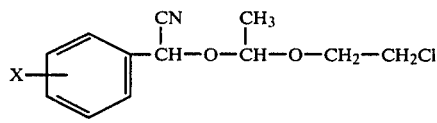

in which X is selected from the group consisting of hydrogen and halogen wherein the halogen is chlorine, bromine or iodine.

This invention also embodies a two-part herbicidal system comprised of:

(a) an herbicidally effective amount of a thiocarbamate compound of the formula:

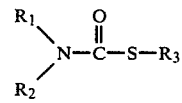

in which $R_1$ is alkyl having 1-6 carbon atoms, inclusive;

$R_2$ is selected from the group consisting of alkyl having 1-6 carbon atoms, inclusive; and cyclohexyl; or $R_1$ and $R_2$ form indistinguishable parts of a single alkylene ring having 4-10 carbon atoms, inclusive; and $R_3$ is selected from the group consisting of alkyl having 1-6 carbon atoms, inclusive; haloalkyl wherein halo is selected from the group consisting of chlorine, bromine and iodine and alkyl has 1-6 carbon atoms, inclusive; alkenyl having 2-6 carbon atoms, inclusive; halo alkenyl wherein halo is selected from the group consisting of chlorine, bromine and iodine and alkenyl has 2-6 carbon atoms, inclusive; benzyl; and halo-substituted benzyl, wherein halo is selected from the group consisting of chlorine, bromine and iodine; and (b) an non-phytotoxic antidotally effective amount of a compound of the formula

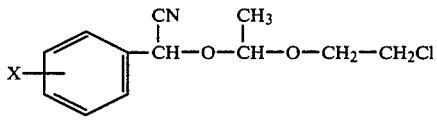

in which X is selected from the group consisting of hydrogen and halogen wherein the halogen is chlorine, bromine or iodine.

By way of exemplification, the active thiocarbamate herbicides employed in the invention may include: S-ethyl N,N-dipropyl thiocarbamate, S-ethyl N,N- diisobutyl thiocarbamate, S-propyl N,N-dipropyl thiocarbamate, S-propyl N-butyl-N-ethylthiocarbamate, S-(2,3,3-tri-chloroallyl)diisopropyl thiocarbamate, S-ethyl N-ethyl N-cyclohexyl thiocarbamate, S-ethyl hexahydro-1H-azepine-1-carbothioate, isopropyl hexahydro-1,4azepine-1-carbothioate, S-benzyl N,N-disecbutylthiolcarbamate, S-(4-chlorobenzyl)N,N-diethyl thiolcarbamate and combinations thereof.

This invention also embodies a two-part herbicidal system comprised of (a) an herbicidally effective amount of an acetanilide compound of the formula

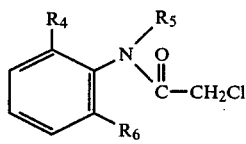

in which $R_4$ and $R_6$ are independently selected from the group consisting of hydrogen; and alkyl having 1–6 carbon atoms, inclusive; and $R_5$ is selected from the group consisting of alkyl having 1–6 carbon atoms, inclusive; alkoxy having 1–8 carbon atoms, inclusive; and carbethoxyalkyl wherein the alkyl group has 1–4 carbon atoms, inclusive; and (b) an non-phytotoxic antidotally effective amount of a compound of the formula

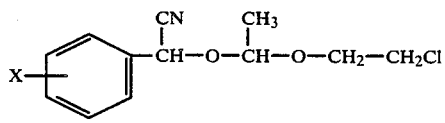

in which X is selected from the group consisting of hydrogen and halogen wherein the halogen is chlorine, bromine or iodine.

By way of exemplification, the active acetanilide compounds employed in the invention may include: 2-chloro-2',6'-diethyl-N-(methoxymethyl)acetanilide; 2-chloro-2'-methyl-6'-ethyl-N(methoxypropyl-(2))-acetanilide; 2-chloro-2',6'-dimethyl-N-(methoxyethyl)acetanilide; 2-chloro-2'-methyl-6'-ethyl-N-(ethoxymethyl)acetanilide; 2-chloro-N-isopropyl acetanilide; 2-chloro-2',6'-diethyl-N-(n-butoxymethyl)acetanilide; and 2-chloro-N-carbethoxymethyl-2',6'diethyl acetanilide.

This invention also includes the method of establishing herbicidal selectivity which comprises applying to the locus where selectivity is desired an antidotally effective amount of a compound of the formula

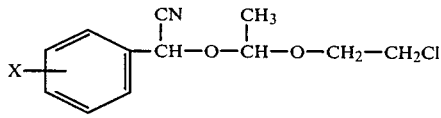

in which X is selected from the group consisting of hydrogen and halogen wherein the halogen is chlorine, bromine or iodine.

The locus where selectivity is desired may include soil, seeds, seedlings, and vegetation.

Preparation

The thiocarbamates of the present composition are either commercially available or can be prepared by the procedures described in U.S. Pat. Nos. 2,913,327; 2,983,747; 3,133,947; 3,185,720; and 3,198,786.

The acetanilides of the present composition are either commercially available or can be prepared by the procedures described in U.S. Pat. Nos. 2,863,752; 3,442,945; 3,780,090; 3,937,730; 3,952,056; and 4,070,179.

The substituted benzyloxy chloroethoxy ethane compounds of the present invention can be prepared according to the following procedure, depending on the starting materials.

EXAMPLE I

STEP 1: Preparation of 2-chlorobenzaldehyde cyanohydrin

Seventy grams (g) (0.5 mole) of 2-chlorobenzaldehyde, 34 g (0.69 mole) of sodium cyanate, 250 milliliters (ml) $H_2O$, and 50 ml tetrahydrofuran (THF) were combined in a reaction flask. The mixture was cooled in an ice bath and 35 g (0.35 mole) of concentrated sulfuric acid was added slowly such that the reaction temperature did not rise above 20° C. The reaction mixture was stopped and stirred at room temperature for 48 hours. Two hundred ml of ether was added, the layers were separated, and the organic layer was dried and stripped. Yield was 87.5 g of 3-chlorobenzaldehyde cyanohydrin. Structure was confirmed by infrared, nuclear magnetic resonance and mass spectroscopy.

STEP 2: Preparation of 1-α-cyano-2-chlorobenzyloxy-1-(2-chloroethoxy)ethane

Thirty-three g (0.2 mole) of 2-chlorobenzaldehyde cyanohydrin were combined with 21 ml (0.21 mole) of 2-chloroethyl vinylether and 30 ml of dry THF. The solution was cooled to 10° C. and 0.5 g of methane sulfonic acid was added. The solution was stirred cold for 3 hours and 500 ml of ether was added. The ether solution was washed with dilute caustic, dried and stripped. Yield was 49.7 g of 1-α-cyano-2-chlorobenzyloxy-1-(2-chloroethoxy)ethane. Structure was confirmed by infrared, nuclear magnetic resonance and mass spectroscopy.

The compounds prepared according to this procedure appear in Table I.

TABLE I

Substituted Benzyloxy Chloroethoxy Ethane

| Cmpd. No. | X | Chemical Name | Physical Constant |
|---|---|---|---|
| 1 | H | 1-α-cyanobenzyloxy-1-(2-chloroethoxy) ethane | $n_D^{30} = 1.4750$ |
| 2 | Cl | 1-α-cyano-2-chlorobenzyloxy-1-(2-chloroethoxy) ethane | $n_D^{30} = 1.5135$ |

Testing

Stock solutions of the herbicides were prepared by diluting the requisite amount of each herbicide in water or a 1:1 solution of water and acetone. Examples of solutions, compositions, and application rates are summarized in Table II.

TABLE II

| Herbicide Name | Herbicide Stock Solutions | | | | |
|---|---|---|---|---|---|
| | Composition | | | Application | |
| | Herbicide (mg)* | Water (ml) | Acetone (ml) | ml/flat** | lb/acre |
| VERNAM ® 6E S—propyl-N,N—dipropyl thiocarbamate | 427 | 400 | 0 | 5 | 1.00 |
| | 2560 | 400 | 0 | 5 | 6.00 |
| EPTAM ® TECH S—ethyl-N,N—dipropyl thiocarbamate | 2400 | 500 | 0 | 5 | 6.00 |
| LASSO ® 4E 2-chloro-2',6'-diethyl-N—(methoxymethyl) acetanilide | 7656 | 350 | 350 | 2.7 | 3.50 |
| TERIDOX ® TECH 2-chloro-2',6'-dimethyl-N—(methoxyethyl) acetanilide | 1050 | 350 | 350 | 2.7 | 1.00 |

*The weight is measured in terms of mg of herbicide formulated as indicated. The VERNAM ® 6E formulation has about 72% active herbicide compound, EPTAM ® TECH and TERIDOX ® TECH are 100% active herbicide compound, and LASSO ® 4E has about 48% active herbicide compound.
**The flats measure 5.95 inches by 9.5 inches. Approximately four (4) mg/flat is equal to one (1) lb/acre.

The herbicide was either incorporated into the soil prior to planting or applied to the soil after planting and prior to emergence of the plants. In some cases of pre-plant incorporation, the herbicide was incorporated into the soil alone in preparation for in-furrow application of the antidote; in others the herbicide solution was tank-mixed with the antidote solution prior to incorporation.

Stock solutions of each antidote compound were prepared at the desired concentrations by diluting the requisite amounts of each antidote in acetone. An example of a solution composition, rate and application method is summarized in Table III.

TABLE II

| Antidote Stock Solutions | | | | |
|---|---|---|---|---|
| Antidote: Substituted benzyloxy chloroethoxy ethanes | | | | |
| Composition | | Application | | |
| Antidote (mg) | Acetone (ml) | ml/flat | lb/acre | Method |
| 95 | 15 | 1.50 | 5.00 | IF* |

*IF = In-furrow surface application of antidote.

The antidote solutions were applied to the soil either by infurrow surface application, or by pre-plant incorporation. In all cases of pre-plant incorporation, the antidote was tank-mixed with the herbicide prior to incorporation into the soil.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only. All flats were placed on greenhouse benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2-dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the control flats.

The treated crops initially screened for herbicidal injury were milo, wheat, cotton, rice, barley, corn and soybeans. The compound was tested on the weed species watergrass (*Echinochloa crusgalli*) and foxtail (*Setaria viridis*).

| KEY TO TABLES IV AND V |
|---|
| Herbicides |
| VERNAM ® - S—propyl-N,N—di-propyl thiocarbamate |
| EPTAM ® - S—ethyl-N,N—dipropyl thiocarbamate |
| LASSO ® - 2-chloro-2',6'-diethyl-N—(methoxymethyl) acetanilide |
| TERIDOX ® - 2-chloro-2',6'-diethyl-N—(methoxymethyl) acetanilide |
| Application Methods |
| PES = Surface application of herbicide to soil after planting of seeds and prior to emergence of plants. |
| IF = In-furrow surface application of antidote (soil previously treated with herbicide only). |
| PPI = Pre-plant incorporation of herbicide or antidote. If both herbicide and antidote were preplant incorporated, a tank-mixed solution was used. |
| TM = Tank mixed solution of herbicide and antidote. |

If no antidote was applied, the word "none" appears in the Antidote Rate column. These are the control flats for each crop. The results shown on this line are the percent injuries sustained by each of the crops when treated with the herbicide only at the rate specified.

All rates shown, for both herbicide and antidote, are in pounds per acre.

Injury Ratings

The injury to the crop (Table IV) or weeds (Table V) is shown as a percentage of damage done to the plants as compared to an evaluation of the overall undamaged state of the plants. The damage done to the plants is a function of the number of plants injured and the extent of injury to each plant. This rating is made four (4) weeks after application of the herbicide alone or of the herbicide in combination with the antidote.

An asterisk (*) in Table IV indicates that the antidote compound is active in reducing herbicidal injury to the crop.

Table V shows that the antidote compound has no effect on weeds, i.e., herbicidal injury to the weeds is sustained even in the presence of the antidote compound.

TABLE IV

Antidotal Effectiveness

| Cmpd. No. | Herbicide | Herbicide Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
| 1 | VERNAM | 1.25 | PPI | none | — | 96 | 98 | 60 | 95 | 85 | | |
|   | VERNAM | 1.25 | PPI | 5.00 | IF | *65 | *90 | 60 | 95 | *60 | | |
|   | VERNAM | 6.00 | PPI | none | — | | | | | | 90 | 65 |
|   | VERNAM | 6.00 | PPI | 5.00 | IF | | | | | | *10 | 65 |
|   | EPTAM | 6.00 | PPI | none | — | | | | | | 90 | |
|   | EPTAM | 6.00 | PPI/TM | 0.0025 | PPI/TM | | | | | | 90 | |
|   | EPTAM | 6.00 | PPI/TM | 0.025 | PPI/TM | | | | | | 90 | |
|   | EPTAM | 6.00 | PPI/TM | 0.05 | PPI/TM | | | | | | 90 | |
|   | EPTAM | 6.0 | PPI | none | — | | | | | | 75 | |
|   | EPTAM | 6.0 | PPI/TM | 0.05 | PPI/TM | | | | | | 75 | |
|   | EPTAM | 6.0 | PPI/TM | 0.50 | PPI/TM | | | | | | *55 | |
|   | EPTAM | 6.0 | PPI/TM | 5.00 | PPI/TM | | | | | | *0 | |
|   | LASSO | 3.50 | PES | none | — | 95 | 70 | | 100 | 70 | | |
|   | LASSO | 3.50 | PES | 5.00 | IF | *90 | 70 | | 100 | *60 | | |
|   | TERIDOX | 1.00 | PES | none | — | 100 | 70 | | | 80 | 100 | |
|   | TERIDOX | 1.00 | PES | 5.00 | IF | 100 | 70 | | | 80 | *90 | |
| 2 | VERNAM | 1.00 | PPI | none | — | 100 | 100 | 40 | 95 | 90 | | |
|   | VERNAM | 1.00 | PPI | 5.00 | IF | 100 | 100 | 40 | 95 | 90 | | |
|   | VERNAM | 6.00 | PPI | none | — | | | | | | 90 | 60 |
|   | VERNAM | 6.0 | PPI | 5.00 | IF | | | | | | *30 | 60 |
|   | EPTAM | 6.00 | PPI | none | — | | | | | | 90 | |
|   | EPTAM | 6.00 | PPI/TM | 0.05 | PPI/TM | | | | | | 90 | |
|   | EPTAM | 6.00 | PPI/TM | 5.00 | PPI/TM | | | | | | 45 | |
|   | LASSO | 3.50 | PES | none | — | 95 | 70 | | 100 | 70 | | |
|   | LASSO | 3.50 | PES | 5.00 | IF | *60 | *40 | | *95 | 70 | | |
|   | TERIDOX | 1.00 | PES | none | — | 100 | 70 | | | 80 | 100 | |
|   | TERIDOX | 1.00 | PES | 5.00 | IF | 100 | *45 | | | 80 | *85 | |

TABLE V

Herbicidal Effectiveness

| Cmpd. No. | Herbicide Name | Rate | Herbicide Method | Antidote Rate | Antidote Method | Watergrass | Foxtail |
|---|---|---|---|---|---|---|---|
| 1 | EPTAM | 6.00 | PPI | none | — | 100 | 100 |
|   | EPTAM | 6.00 | PPI/TM | 0.0025 | PPI/TM | 100 | 100 |
|   | EPTAM | 6.00 | PPI/TM | 0.025 | PPI/TM | 100 | 100 |
|   | EPTAM | 6.00 | PPI/TM | 0.50 | PPI/TM | 100 | 100 |
|   | EPTAM | 6.00 | PPI | none | — | 100 | 100 |
|   | EPTAM | 6.00 | PPI/TM | 0.05 | PPI/TM | 100 | 100 |
|   | EPTAM | 6.00 | PPI/TM | 0.50 | PPI/TM | 100 | 100 |
|   | EPTAM | 6.00 | PPI/TM | 5.00 | PPI/TM | 100 | 100 |
|   | LASSO | 3.50 | PES | none | — | 100 | |
|   | LASSO | 3.50 | PES | 5.00 | IF | 100 | |
|   | TERIDOX | 1.00 | PES | none | — | 100 | |
|   | TERIDOX | 1.00 | PES | 5.00 | IF | 100 | |
| 2 | EPTAM | 6.00 | PPI | none | — | 100 | 100 |
|   | EPTAM | 6.00 | PPI/TM | 0.50 | PPI/TM | 100 | 100 |
|   | EPTAM | 6.00 | PPI/TM | 5.00 | PPI/TM | 100 | 100 |
|   | LASSO | 3.50 | PES | none | — | 100 | |
|   | LASSO | 3.50 | PES | 5.00 | IF | 100 | |
|   | TERIDOX | 1.00 | PES | none | — | 100 | |
|   | TERIDOX | 1.00 | PES | 5.00 | IF | 100 | |

Test Results

The substituted benzyloxy chloroethoxy ethane compounds show good antidotal activity for a variety of crops. They are effective as an antidote with both thiocarbamate and acetanilide herbicides. Use of these compounds did not result in a reduction of herbicidal injury weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, Pesticide Formulations (Marcel Dekker, Inc., N.Y., 1973) at pages 79-84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A herbicidal composition for use on wheat comprising:
   (a) an herbicidally effective amount of an acetanilide compound of the formula

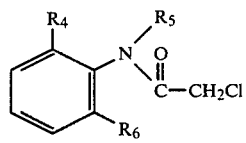

in which $R_4$ and $R_6$ are independently alkyl having 1-2 carbon atoms, inclusive; and $R_5$ is alkoxyalkyl having 2-4 carbon atoms, inclusive; and (b) a non-phytotoxic antidotally effective amount of a compound of the formula

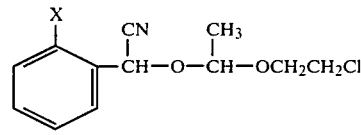

in which X is chlorine, bromine or iodine.

2. A composition as defined in claim 1 wherein X is chlorine.

3. A composition as defined in claim 1 wherein $R_4$ and $R_6$ are both ethyl and $R_5$ is methoxymethyl.

4. A composition as defined in claim 1 wherein $R_4$ and $R_6$ are both methyl and $R_5$ is methoxyethyl.

5. A method of controlling undesirable vegetation and reducing herbicidal injury to wheat due to an acetanilide herbicide which comprises applying to the locus where control is desired a herbicidal composition comprising:
   (a) an herbicidally effective amount of an acetanilide compound of the formula

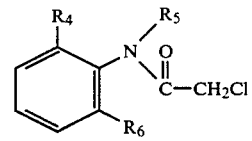

in which $R_4$ and $R_6$ are independently alkyl having 1-2 carbon atoms, inclusive; and $R_5$ is alkoxyalkyl having 2-4 carbon atoms, inclusive; and (b) a non-phytotoxic antidotally effective amount of a compound of the formula

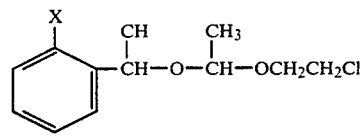

in which X is chlorine, bromine or iodine.

6. A method as defined in claim 5 wherein X is chlorine.

7. A method as defined in claim 5 wherein $R_4$ and $R_6$ are both ethyl and $R_5$ is methoxymethyl.

8. A method as defined in claim 5 wherein $R_4$ and $R_6$ are both methyl and $R_5$ is methoxyethyl.

* * * * *